United States Patent [19]

Uda et al.

[11] Patent Number: 5,115,097
[45] Date of Patent: May 19, 1992

[54] SYNTHETIC PEPTIDE FROM THE CARBOXY TERMINAL OF HUMAN MN-SUPEROXIDE DISMUTASE

[75] Inventors: Taizo Uda; Akira Takeyasu; Tetsuo Kawaguchi; Yukio Nakajima, all of Ube, Japan

[73] Assignee: Ube Industries, Ltd., Ube, Japan

[21] Appl. No.: 395,010

[22] Filed: Aug. 17, 1989

[30] Foreign Application Priority Data

Sep. 21, 1988 [JP] Japan ................. 63-234824

[51] Int. Cl.⁵ .................. A61K 37/02; C07K 7/06; C07K 7/08; C07K 7/10
[52] U.S. Cl. .................................... 530/326; 530/327
[58] Field of Search ................. 530/327, 326; 514/13, 514/14, 15

[56] References Cited

U.S. PATENT DOCUMENTS 3,531,258  9/1970  Merrifield et al. ................. 530/334

OTHER PUBLICATIONS

Beck et al., Efficient Production of Active Human Manganese Superoxide Dismutase in *Escherichica coli;* Bio/technology; vol. 6; 1988.

Kawaguchi et al., "A monoclonal antibody against COOH-terminal peptide of human liver manganese superoxide dismutase", J. Biol. Chem. 264, 5762-5767, 1989.

Barra et al., "The Primary Structure of Human Liver Manganese Superoxide Dismutase", J. Biol. Chem., 259, 12595-12601, 1984.

*Primary Examiner*—Lester L. Lee
*Assistant Examiner*—S. G. Marshall
*Attorney, Agent, or Firm*—Foley & Lardner

[57] ABSTRACT

Monomeric synthetic peptide and dimeric synthetic peptide comprising an amino acid sequence represented by the formula:

X-Asn-Val-Thr-Glu-Arg-Tyr-Met-Ala-Cys-Lys-Lys wherein

X represents a residue comprising 0 to 10 amino acids sequence; and Asn represents aspartic acid, Val valine, Thr threonine, Glu glutamic acid, Arg arginine, Tyr tyrosine, Met methionine, Ala alanine, Cys cysteine and Lys lysine;

an assay kit of human Mn-SOD to be used in the assay method of human Mn (manganese)-SOD comprising as essential components:

(a) at least one of the above monomeric and dimeric synthetic peptides; and
(b) an enzyme-labelled monoclonal antibody having a very high specific immunoreactivity against at least one of the above monomeric and dimeric synthetic peptides and at the same time having a very high specific immunoreactivity against human Mn-SOD; and an assay method of human Mn-SOD, which comprises immobilizing at least one of the above monomeric and dimeric synthetic peptides on a carrier, then allowing human Mn-SOD in a sample to be measured and the immobilized synthetic peptide to react competitively with the enzyme-labelled monoclonal antibody having a very high specific immunoreactivity against at least one of the above monomeric and dimeric synthetic peptides and at the same time having a very high specific immunoreactivity against human Mn-SOD; and thereby preparing an enzyme-labelled complex comprising the synthetic peptide immobilized on the carrier and the enzyme-labelled monoclonal antibody.

2 Claims, 10 Drawing Sheets

SYNTHETIC PEPTIDE FROM THE CARBOXY TERMINAL OF HUMAN MN-SUPEROXIDE DISMUTASE

BACKGROUND OF THE INVENTION

This invention relates to a synthetic peptide, an assay kit and an assay method of human Mn (manganese)-superoxide dismutase (hereinafter abbreviated as Mn-SOD) by use thereof.

Human Mn-SOD is an enzyme (with a molecular weight of one domain being about 25,000, and considered to comprise dimer or tetramer thereof) existing in the matrix portion of mitochondria, and catalyzes the reaction which disproportionate the superoxide anion radical ($O_2^-$) which is the primary molecular species of active oxygen as shown below:

$$2\,O_2^- + 2\,H^+ \rightarrow H_2O_2 + O_2$$

Whereas, measurement of human Mn-SOD concentration of serum in liver diseases has been considered to be of high diagnostic significance according to the investigations by use of polyclonal antibodies (Pharmaceutical Journal: Inagaki, Sawaki, 20, 1, 1984; The 5th Tumor Marker Research Meeting: Iizuka, Arai et al, 1985). Also, Taniguchi et al have shown that human Mn-SOD concentration is higher in lung cancer according to the immunological method by use of a polyclonal antibody prepared by immunization of a goat (Journal of National Cancer Institute, 72, 5, 1984). Thus, importance of human Mn-SOD concentration in serum has been pointed out.

Accordingly, for assaying human Mh-SOD concentration in serum, it has been required that human Mn-SOD can be assayed inexpensively, simply and at high sensitivity by use of an enzyme-labelled monoclonal antibody having high specific reactivity against human Mn-SOD, a peptide capable of reacting competitively with human Mn-SOD against the monoclonal antibody, and human serum, in place of the use of the polyclonal antibody against human Mn-SOD of the prior art. However, no such assay method has been known.

SUMMARY OF THE INVENTION

An object of the present invention is to provide a synthetic peptide, an assay kit and an assay method of human Mn-SOD by use thereof.

The present inventors have intensively studied in order to solve the above problems, and consequently found that human Mn-SOD can be measured easily and at high sensitivity by assaying human Mn-SOD by use of an assay kit of human Mn-SOD, to accomplish the present invention.

More specifically, the present invention concerns:

(1) a monomeric or dimeric synthetic peptide comprising an amino acid sequence represented by the formula:

X-Asn-Val-Thr-Glu-Arg-Tyr-Met-Ala-Cys-Lys-Lys wherein X represents a residue comprising 0 to 10 amino acids sequence; and Asn represents aspartic acid, Val valine, Thr threonine, Glu glutamic acid, Arg arginine, Tyr tyrosine, Met methionine, Ala alanine, Cys cysteine and Lys lysine;

(2) an assay kit of human Mn-SOD to be used in the assay method of human Mn-SOD comprising as essential components:

(a) at least one of the above monomeric and dimeric synthetic peptides; and (b) an enzyme-labelled monoclonal antibody having a very high specific immunoreactivity against at least one of the above monomeric and dimeric synthetic peptides and at the same time having a very high specific immunoreactivity against human Mn-SOD; and (3) an assay method of human Mn-SOD, which comprises immobilizing at least one of the above monomeric and dimeric synthetic peptides on a carrier, then allowing human Mn-SOD in a sample to be measured and the immobilized synthetic peptide to react competitively with the above enzyme-labelled monoclonal antibody having a very high immunoreactivity against at least one of the above monomeric and dimeric synthetic peptides and at the same time having a very high immunoreactivity against human Mn-SOD, thereby preparing an enzyme-labelled complex comprising the synthetic peptide immobilized on the carrier and the enzyme-labelled monoclonal antibody.

DESCRIPTION OF THE PREFERRED EMBODIMENTS

The present invention will be described in detail below.

The assay kit of human Mn-SOD to be used in the assay method of human Mn-SOD of the present invention comprises as essential components at least one of monomeric and dimeric synthetic peptides comprising the amino acid sequence on the carboxyl end (C-end) side of human Mn-SOD (hereinafter monomeric and dimeric synthetic peptides are abbreviated comprehensively as "synthetic peptide"), and an enzyme-labelled monoclonal antibody having a very high specific immunoreactivity against the "synthetic peptide" and at the same time having a very high specific immunoreactivity against human Mn-SOD. When a monoclonal antibody not labelled with an enzyme is used, by use of an enzyme-labelled antibody which can react specifically with the monoclonal antibody, the same object as in the present invention can be accomplished. The antibody in this enzyme-labelled antibody is not particularly limited, provided that it can react specifically with the monoclonal antibody.

In the assay method of human Mn-SOD of the present invention, in addition to these reagents, a carrier, a washing solution, a blocking solution, human Mn-SOD solutions of known concentrations for preparation of human Mn-SOD standard curves (hereinafter abbreviated as "standard human Mn-SOD solution"), substrate solutions corresponding to enzyme-labelled complexes (hereinafter abbreviated as "substrate solution"), etc. are also required, and these may be assembled preliminarily in the assay kit of human Mn-SOD, or may be also prepared before assay. When the carrier is to be assembled previously in the assay kit of human Mn-SOD, the "synthetic peptide" can be also previously immobilized on the carrier.

The enzyme-labelled complex in the present invention is "one comprising the "synthetic peptide" immobilized on a carrier, said enzyme-labelled monoclonal antibody" which is formed by having the "synthetic peptide" immobilized on a carrier and allowing the immobilized "synthetic peptide" or the human Mn-SOD in a sample to be measured to react competitively with said monoclonal antibody. When a monoclonal antibody not labelled with an enzyme is used, the same object as in the present invention can be accomplished by use of an enzyme-labelled antibody capable of reacting specifically with the monoclonal antibody. The enzyme-labelled complex formed in such case comprises "one comprising the "synthetic peptide" immobilized on a carrier, a monoclonal antibody and an enzyme-labelled antibody".

The monomeric synthetic peptide of the present invention can be synthesized according to conventional methods such as the liquid phase method, the solid phase method and the like, but preferably synthesized according to the solid phase method by bonding successively the amino acids corresponding to the peptide fragment on the C-end (carboxyl end) side of human Mn-SOD from the C-end side through peptide bonding onto a polymeric solid phase support.

On the other hand, its dimeric synthetic peptide can be synthesized by maintaining the solution of the monomeric peptide obtained as described above as such in neutral or alkaline state, or converting it into acidic state.

The "synthetic peptide" thus obtained can be purified according to conventional method such as high performance liquid chromatography (HPLC) by use of a reverse phase system column, and its amino acid sequence can be identified by amino acid analysis.

The number of amino acid residues in the monomeric synthetic peptide of the present invention is not particularly limited, provided that the monomeric synthetic peptide immobilized on a carrier can react with said enzyme-labelled monoclonal antibody to form an enzyme-labelled complex in the assay method of human Mn-SOD of the present invention, but may be preferably 11 residues or more, and its amino acid residue number may be preferably 11 to 21 residues.

As such monomeric synthetic peptide, those corresponding to 11 to 21 amino acid residue portions from the C-end of human Mn-SOD, for example, Asn-Val-Thr-Glu-Arg-Tyr-Met-Ala-Cys-Lys-Lys, Ile-Asn-Trp-Glu-Asn-Val-Thr-Glu-Arg-Tyr-Met-Ala-Cys-Lys-Lys, and Lys-Ala-Ile-Trp-Asn-Val-Ile-Asn-Trp-Glu-Asn-Val-Thr-Glu-Arg-Tyr-Met-Ala-Cys-Lys-Lys, wherein
Asn, Val, Thr, Glu, Arg, Tyr, Met, Ala, Cys and Lys are as defined above and Ile represents isoleucine and Trp represents tryptophan,
can be included.

The amino acid sequence of the monomeric synthetic peptide may also be substituted with other amino acid residues, provided that a monoclonal antibody exhibiting antigen-antibody reaction with the peptide containing the 11 to 20 residues from the C-end of human Mn-SOD is used.

As the "synthetic peptide" in the present invention, the above various monomeric synthetic peptides or dimers thereof can be used either singly or in combination.

The monoclonal antibody in the present invention is not particularly limited, provided that it exhibits specific antigen-antibody reaction with the "synthetic peptide", but it is preferable to use a monoclonal antibody capable recognizing specifically the "synthetic peptide", for example, the product (PG11) produced by a PG11 cell line (FERM-P No. 1608) which is a hybridoma cell line prepared by cell fusion of lymphocytes of an immunized mouse and mouse myeloma cells. The purity of such monoclonal antibody should be preferably of high purity purified by salting out by use of ammonium sulfate or ion exchange chromatography. If necessary, to the monoclonal antibody, there may be also added a preservative of protein such as sodium azide, sodium ethylmercurithiosalicylate in necessary amount.

In preparation of the enzyme-labelled monoclonal antibody in the assay kit of human Mn-SOD of the present invention, as the enzyme for labelling the monoclonal antibody, there may be employed at least one selected from redox system enzymes such as peroxidase, catalase, glucoseoxidase, lactateoxidase, alcoholoxidase, monoamineoxidase, $\beta$-galactosidase, etc. and phosphate hydrolases such as alkali phosphatase, etc.

Preparation of the enzyme-labelled monoclonal antibody in the present invention can be performed by bonding the above monoclonal antibody and at least one enzyme as mentioned above according to the one step method by use of glutaraldehyde (Immunochemistry, 6, 43 (1969)) or the two-step method (Immunochemistry, 8, 1175 (1971)), the periodic acid oxidation method (Method in Enzymology, 37, 133 (1975)) or the maleimide method (Journal of the Biochemistry], 78, 235 (1975)), but it is preferable to use either one of the latter two methods.

This can be also used as such as the enzyme-labelled monoclonal antibody, but it is preferable to use the product obtained by purification of this according to gel filtration by use of Sephadex, Sephacryl, etc. as the enzyme-labelled monoclonal antibody for the purpose of enhancing further the assay sensitivity of human Mn-SOD.

The enzyme-labelled monoclonal antibody fraction obtained by such gel filtration can be also used as such (if the protein concentration is low, concentrated to a desired concentration by dialysis membrane, etc., while if the protein concentration is high, diluted to a desired concentration), but it may be preferably dialyzed with a buffer (e.g. phosphate buffer (PBS), or Tris-HCl buffer) which has been controlled to a pH around neutral, lyophilized or filtered with a microorganism eliminating filter for storage, and if necessary formed into an enzyme-labelled monoclonal antibody solution at a protein concentration of 0.01 to 100 $\mu$g/ml, preferably 0.1 to 10 $\mu$g/ml before use. Also, if necessary, to the enzyme-labelled monoclonal antibody a preservative of protein such as sodium azide, sodium ethylmercurithiosalicylate can be added in necessary amount to an extent where no adverse influence is given on the measurement of the enzymatic activity.

A known amount of human MN-SOD to be used for preparation of the calibration curve of human Mn-SOD of the present invention ("standard human Mn-SOD solution") can be obtained by purification by heat treatment, ammonium sulfate fractionation, ion exchange chromatography, gel filtration, isoelectric point chromatography, etc. according to Journal of National Cancer Institute, 72, 5, (1984).

The carrier to be used in assay of human Mn-SOD of the present invention is required as the carrier for immobilizing the "synthetic peptide" in the assay kit of human Mn-SOD.

Examples of the shape of the carrier which can be used for immobilizing the "synthetic peptide" in the present invention may include plate, tube, beads, membrane for immunoassay, and examples of the material may include, for example, polyethylene, polystyrene, polypropylene, nitrocellulose, glass, etc.

The washing solution to be used in assay of human Mn-SOD in the present invention is required for washing away those not immobilized on the carrier after immobilizing a predetermined amount of the "synthetic peptide" on the carrier, or for washing away the unreacted substances after the reaction of the "synthetic peptide" immobilized on the carrier with said enzyme-labelled monoclonal antibody.

As the washing solution to be used for such purpose, there can be employed water, a buffer adjusted to the pH during the reaction (buffer such as phosphate buffer and Tris-HCl buffer), the above buffer containing 0 to 3 vol. % of a surfactant such as Tween 20, Tween 60, etc., preferably a buffer adjusted to the pH during the reaction containing 0.02 to 0.8 vol. % of the above surfactant.

The blocking solution to be used in the assay of human Mn-SOD of the present invention is required for preventing nonspecific bonding of human Mn-SOD, said enzyme-labelled monoclonal antibody onto the carrier surface, and also can be used as the solvent when preparing a diluted solution of an assay sample.

The blocking solution to be used for such purpose can be prepared by dissolving macromolecular proteins such as bovine serum albumin (BSA), ovalbumin (OVA), keyhole limpet hemocyanine (KLH), $\gamma$-globulin, etc., sera of various animals in the above washing solution adjusted to the pH during the reaction, and the concentration of these macromolecular proteins should be preferably made 0.1 to 10 wt./vol. %, preferably 0.1 to 2 wt./vol. %, and when it is prepared by use of sera of various animals, the concentration should be preferably made 1 to 50 vol./vol. preferably 10 to 20 vol./vol. %.

If necessary, it is also possible to add a preservative of protein such as sodium azide, sodium ethylmercurithiosalicylate in necessary amount.

As the sample to be assayed in the assay of human Mn-SOD of the present invention, human blood fluid such as human urine, blood, serum, etc. itself or these assay samples diluted appropriately with the above washing solution to the range at which human Mn-SOD can be assayed can be used.

As the substrate solution for the enzyme to be used in the assay of human Mn-SOD of the present invention ("substrate solution"), there can be used a buffer containing o-phenylenediamine, 2,2'-aminobis(3-ethylbenzothiazoline-6-sulfonic acid (ABTS), etc. which can indicate a color with the substance formed by the enzymatic reaction when the substrate with which the enzyme used for labelling said monoclonal antibody in said enzyme-labelled monoclonal antibody is $H_2O_2$, or when the substrate is p-nitrophenylphosphate, a buffer containing a substance such as diethanolamine, etc can be used.

As described above, the carrier, the washing solution, the blocking solution, the "standard human Mn-SOD solution", the "substrate solution" are prepared, and by use of the "synthetic peptide", said enzyme-labelled monoclonal antibody which are the assay kit of human Mn-SOD, the human Mn-SOD in an assay sample can be assayed via the respective assay operation steps according to the methods as described below.

(1) The step of immobilizing a predetermined amount of the "synthetic peptide" on a carrier:

A predetermined volume of the "synthetic peptide" solution (the concentration may be, for example, 0.01 to 1 $\mu$g/ml, but preferably 1 $\mu$g/ml or more) is contacted on a given surface area of the carrier for a certain period of time. As the solvent for the "synthetic peptide" solution, an appropriate buffer such as PBS (phosphate buffer), etc., water and others can be used. The reaction temperature is not particularly limited, but preferably 30° to 43° C., more preferably 35° to 40° C. For example, when the temperature is 37° C., it is preferable to effect contact for 15 hours or longer, and contact for 20 hours may be sufficient.

(2) The step of removing the "synthetic peptide" not immobilized on the carrier:

After contacting the "synthetic peptide" with the carrier for a certain time, the "synthetic peptide" solution is removed, and further the residual "synthetic peptide" not immobilized on the carrier is removed by washing for several times with the washing solution.

(3) The step of preventing nonspecific bonding of the sample to be assayed and said enzyme-labelled monoclonal antibody onto the surface of the carrier having no "synthetic peptide" immobilized thereon:

The above carrier having the "synthetic peptide" immobilized thereon obtained in the step (2) is brought into contact with a predetermined volume of a blocking solution for a certain period of time. The temperature during the contact is not particularly limited, but may be preferably 2° to 40° C.

(4) The step of allowing "synthetic peptide" immobilized on the carrier and human Mn-SOD to react competitively with said enzyme-labelled monoclonal antibody, thereby obtaining an enzyme-labelled complex comprising the "synthetic peptide" immobilized on the carrier and said enzyme-labelled monoclonal antibody.

For obtaining an enzyme-labelled complex by allowing the human Mn-SOD in a predetermined volume of the sample to be assayed and said enzyme-labelled monoclonal antibody to react competitively with the above "synthetic peptide" immobilized on the carrier obtained in the step (3), it can be accomplished by allowing a mixture comprising a predetermined volume of the sample to be assayed and the "synthetic peptide" immobilized on the carrier to contact and react with the above "synthetic peptide" immobilized on the carrier obtained in the step of (3) for a certain period of time, and after removal of unreacted solution, removing the residual unreacted solution not immobilized on the carrier through the "synthetic peptide" by washing for several times with the washing solution.

For obtaining an enzyme-labelled complex by use of said monoclonal antibody not labelled with an enzyme, it can be accomplished by allowing a predetermined volume of the sample to be assayed and said monoclonal antibody to contact and react competitively with the above "synthetic peptide" immobilized on the carrier obtained in the step (3) for a certain period of time, and after removal of the unreacted solution, allowing a predetermined volume of an enzyme-labelled antibody capable of reacting specifically with said monoclonal antibody with a predetermined volume of said monoclonal antibody immobilized on the carrier through the "synthetic peptide" for a certain period of time, and after washing away the unreacted solution, removing the unreacted solution remaining without immobilized on the carrier by washing for several times with the washing solution.

(5) The step of removing the unreacted solution of the "synthetic peptide" immobilized on the carrier and said enzyme-labelled monoclonal antibody:

The above unreacted solution in the step (4) is removed by washing for several times with washing the solution.

(6) The step of allowing the enzyme of said enzyme-labelled monoclonal antibody immobilized on the carrier as the enzyme-labelled complex to react with the "substrate solution":

As the "substrate solution" used here, one containing the substrate corresponding to the enzyme used for labelling of said monoclonal antibody in said enzyme-labelled monoclonal antibody and a substance indicating a color through occurrence of the enzymatic reaction is used.

A predetermined volume of the "substrate solution" is allowed to react with said enzyme-labelled monoclonal antibody immobilized on the carrier as the enzyme-labelled complex, and preferably the enzymatic reaction may be stopped by use of an acid such as $H_2SO_4$, an alkali such as NaOH or an enzyme inhibitor.

The reaction temperature may be within the optimum temperature range for the enzyme used without any particular problem, but preferably 20° to 35° C.

(7) The step of measuring absorbance of the reaction mixture after the enzymatic reaction:

The absorbance of the reaction mixture is measured at the wavelength where the color indication of the reaction mixture after the above enzymatic reaction exhibits the maximum absorbance is measured.

As described above, from the results by use of "standard human Mn-SOD solutions" in place of the sample to be assayed, a standard curve is prepared, and the human Mn-SOD content in the sample to be measured can be assayed rapidly and at high sensitivity.

EXAMPLE

The present invention is described in detail by referring to Reference examples and Examples.

These Examples are presented for illustration of the present invention and should not be construed as limitative of the present invention.

REFERENCE EXAMPLE 1

Production and purification of antibody

A PG11 cell line (FERM-P No. 1608) capable of producing a monoclonal antibody having a high specificity for "the synthetic peptide" and at the same time having a very high specificity for human Mn-SOD was cultured, and its $10^7$ cultured cells suspended in a phosphate buffer were administered intraperitoneally into BALB/c mouse (male, 8 weeks old, administered intraperitoneally with 0.5 ml of pristane two weeks before). Remarkable increase of mouse body weight was recognized at around the first week, and ascites was taken out suitably on the first to third weeks. The monoclonal antibody was found to have an antibody titer of $10^6$ to $10^8$.

Purification of the monoclonal antibody from the ascites obtained was carried out as described below.

The above ascites was dialyzed against Tris-HCl buffer (pH 7.4), and passed through a DEAE-cellulose column equilibrated with the same buffer. The fraction passed was salted out with 50% saturated ammonium sulfate, and the precipitates obtained were dissolved in a phosphate buffer (pH 7.4) and dialyzed against the same buffer. The purity of the monoclonal antibody against human Mn-SOD thus obtained was found to be high purity for each antibody by slab gel electrophoresis by use of SDS polyacrylamide gel.

According to the human Mn-SOD assay method (ELISA method) by use of the purified monoclonal antibody (PG11) against said synthetic peptide, it has become possible to assay human Mn-SOD at high sensitivity and rapidly.

EXAMPLE 1

Synthesis of monomeric synthetic peptide comprising 15 amino acid residues

By use of 716 mg of a N-t-butoxycarbonyl-N'-2-chlorobenzyloxycarbonyl lysine resin (lysine content: 0.70 mmol/g, styrene-1%--divinylbenzene copolymer) as the starting material, a synthetic peptide comprising 15 amino acid residues was synthesized according to the solid phase method by use of a peptide automatic synthesizer (manufactured by Applied Biosystems Co. Ltd.). First, a peptide comprising a sequence of 15 amino acids of Ile-Asn-Trp-Glu-Asn-Val-Thr-Glu-Arg- Tyr-Met-Ala-Cys-Lys-Lys (C-end) was allowed to react from the Lys side of its C-end (carboxyl end) successively one by one with the above starting material, thereby obtaining 1.5 g of a protected peptide bonded resin (the amino acids used at this time were protected with benzyl group for Thr, with benzyl ester for Glu, with 2-chlorobenzyloxycarbonyl group for Lys, with formyl group for Trp, with mesitylene-2-sulfonyl group for Arg, with methylsulfoxide group for Met and with S-p-methoxybenzyl group for Cys).

One gram of the protected peptide bonded resin was suspended in a mixture comprising 200 µl of ethanedithiol, 800 µl of m-cresol, 3 ml of dimethylsulfide and 1 ml of trifluoroacetic acid (hereinafter abbreviated as TFA) and stirred at −5° C. for 3 hours. Then, the resin was washed with 5 ml of anhydrous ether for several times, dried under reduced pressure and suspended in a mixture comprising 1 ml of thioanisole and 500 µl of ethanedithiol, followed by stirring at room temperature for 10 minutes. Into the solution was added 10 ml of trifluoroacetic acid under ice-cooling, followed by further stirring at room temperature for 10 minutes. Next, to the mixture was added dropwise 1 ml of trifluoromethanesulfonic acid, followed by stirring at room temperature for 30 minutes and then the product was separated by precipitation with 30 ml of anhydrous ether, washed with anhydrous ether and dried under reduced pressure.

100 mg of the crude synthetic peptide thus obtained were dissolved in 2 ml of distilled water and filtered. The filtrate obtained was placed on AQUAPORE RP-300 (10×100 mm) (Applied Biosystems Co. Ltd.) and eluted by use of a solvent comprising (A) distilled water containing 0.1% TFA and (B) 70% $CH_3CN$ containing 0.1% TFA according to a linear gradient mode of 95-0% of (A) over 60 minutes.

The first of the eluted fractions which exhibited the three great peaks was separated, concentrated and then lyophilized to obtain 15 mg of a monomeric synthetic peptide (a) Ile-Asn-Trp-Glu-Asn-Val-Thr-Glu-Arg-Tyr-Met-Ala-Cys-Lys-Lys.

EXAMPLE 2

Synthesis of dimeric synthetic peptide by use of synthetic peptide of Example 1

A dimeric synthetic peptide (b) could be obtained in an amount of 4 mg by dissolving 5 mg of the monomeric synthetic peptide (a) in Example 1 in a 0.1M phosphate buffer (pH 7.4) (hereinafter abbreviated as PBS) to be placed under the oxidized state.

EXAMPLE 3

Synthesis of monomeric synthetic peptide comprising 21 amino acid residues

First, a peptide comprising a sequence of 21 amino acids of Lys-Ala-Ile-Trp-Asn-Val-Ile-Asn-Trp-Glu-Asn-Val-Thr-Glu-Arg-Tyr-Met-Ala-Cys-Lys-Lys (C-end) was synthesized by linking successively amino acids one by one from the Lys side at its C-end in the same manner as in Example 1 and lyophilized to obtain 20 mg of a monomeric synthetic peptide (c) Lys-Ala-Ile-Trp-Asn-Val-Ile-Asn-Trp-Glu-Asn-Val-Thr-Glu-Arg-Tyr-Met-Ala-Cys-Lys-Lys.

EXAMPLE 4

Synthesis of dimeric synthetic peptide by use of synthetic peptide of Example 3

A dimeric synthetic peptide (d) could be obtained in an amount of 4 mg by dissolving 5 mg of the monomeric synthetic peptide (c) in Example 3 in PBS to be placed under the oxidized state.

EXAMPLE 5

Synthesis of monomeric synthetic peptide comprising 11 amino acid residues

First, a peptide comprising a sequence of 11 amino acids of Asn-Val-Thr-Glu-Arg-Tyr-Met-Ala-Cys-Lys-Lys (C-end) was synthesized by linking successively amino acids one by one from the Lys side at its C-end in the same manner as in Example 1 and lyophilized to obtain 10 mg of a monomeric synthetic peptide (e) Asn-Val-Thr-Glu-Arg-Tyr-Met-Ala-Cys-Lys-Lys.

EXAMPLE 6

Synthesis of dimeric synthetic peptide by use of synthetic peptide of Example 5

A dimeric synthetic peptide (f) could be obtained in an amount of 4 mg by dissolving 5 mg of the monomeric synthetic peptide (e) in Example 5 in PBS to be placed under the oxidized state.

EXAMPLE 6

Preparation of enzyme-labelled monoclonal antibody

As the monoclonal antibody in the enzyme-labelled monoclonal antibody, the purified monoclonal antibody (PG 11) obtained in Reference example was employed.

By use of the monoclonal antibody, this was labelled as described below to obtain the enzyme-labelled monoclonal antibody in the assay kit of the present invention.

First, 8.5 mg of horseradish peroxidase was dissolved in 1 ml of distilled water, 200 µl of sodium periodic acid were added and the mixture was left to stand stationarily at room temperature for 30 minutes. The enzyme solution was dialyzed overnight at 4° C. by use of a 1 mM acetate buffer (pH 4.5), and then 100 µl of 0.2M sodium carbonate buffer (pH 9.5) was added to adjust pH to 9.5.

On the other hand, 8.5 mg of the monoclonal antibody dissolved in 0.1M phosphate buffer (pH 7.4) (PBS) was dialyzed overnight at 4° C. by use of a 0.01M sodium carbonate buffer (pH 9.5). The peroxidase and the monoclonal antibody thus obtained were mixed together, left to stand stationarily at room temperature for 2 hours and half. To the reaction mixture was added sodium tetrahydrideborate, and the mixture was left to stand stationarily at 4° C. for 2 hours. The peroxidase-labelled monoclonal antibody thus obtained was dialyzed overnight under 4° C. by use of PBS, and this was apportioned each in 10 µl into a bottle to provide an enzyme-labelled monoclonal antibody (30 µg/bottle) which is the assay kit of human Mn-SOD. During assay of human Mn-SOD, it was diluted appropriately with PBS before use.

EXAMPLES 7-16

Assay of human Mn-SOD by use of assay kit of human Mn-SOD

Figure 1:
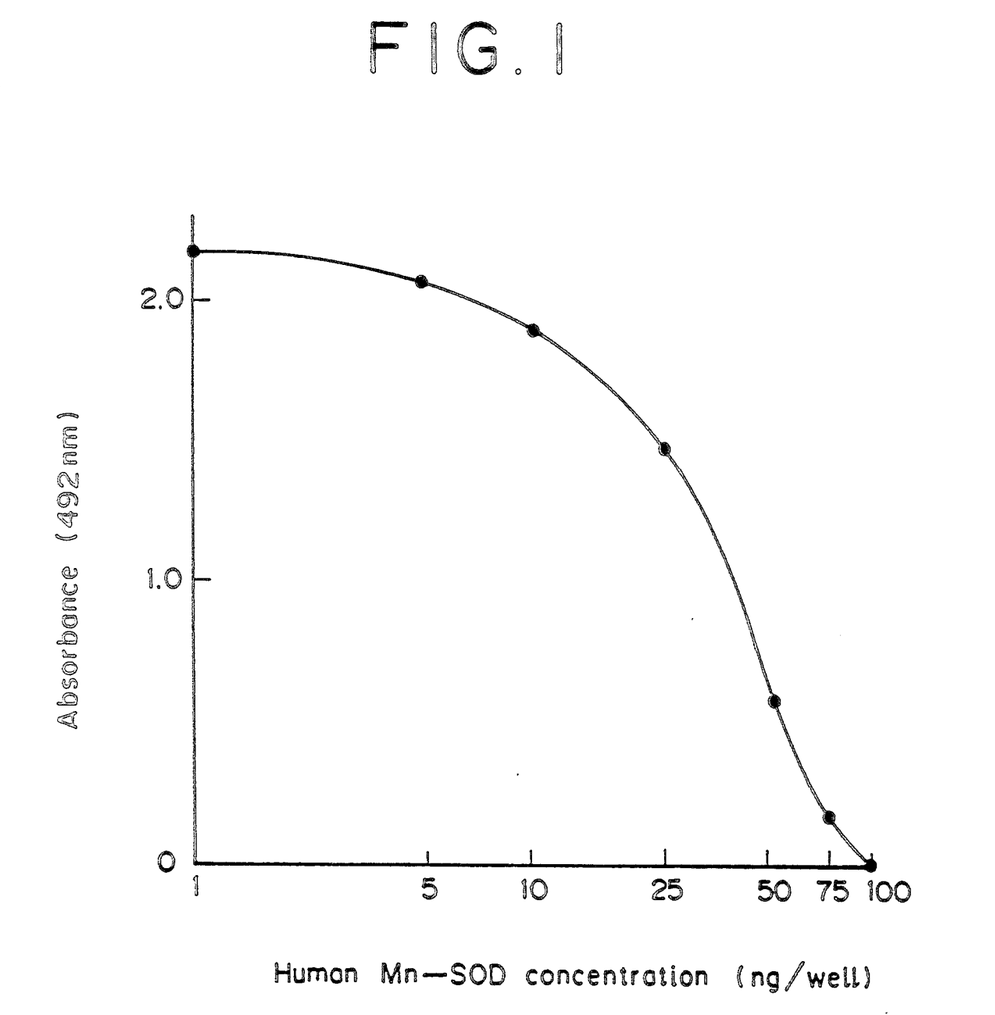
FIG. 1 shows the standard curve of human Mn-SOD prepared by use of the "synthetic peptide" solution A in the assay kit of the present invention in the assay method of human Mn-SOD of the present invention.
Figure 2:
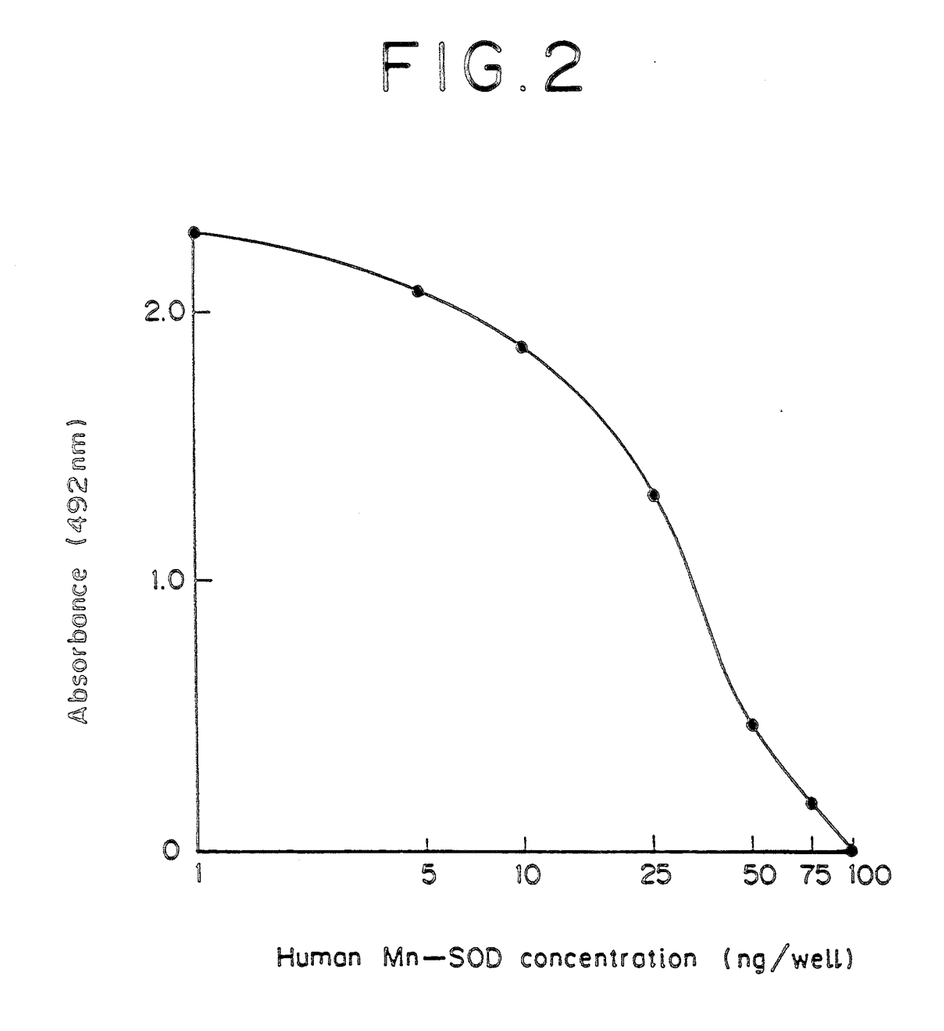
FIG. 2 shows the standard curve of human Mn-SOD prepared by use of the "synthetic peptide" solution B in the assay kit of the present invention in the assay method of human Mn-SOD of the present invention.
Figure 3:
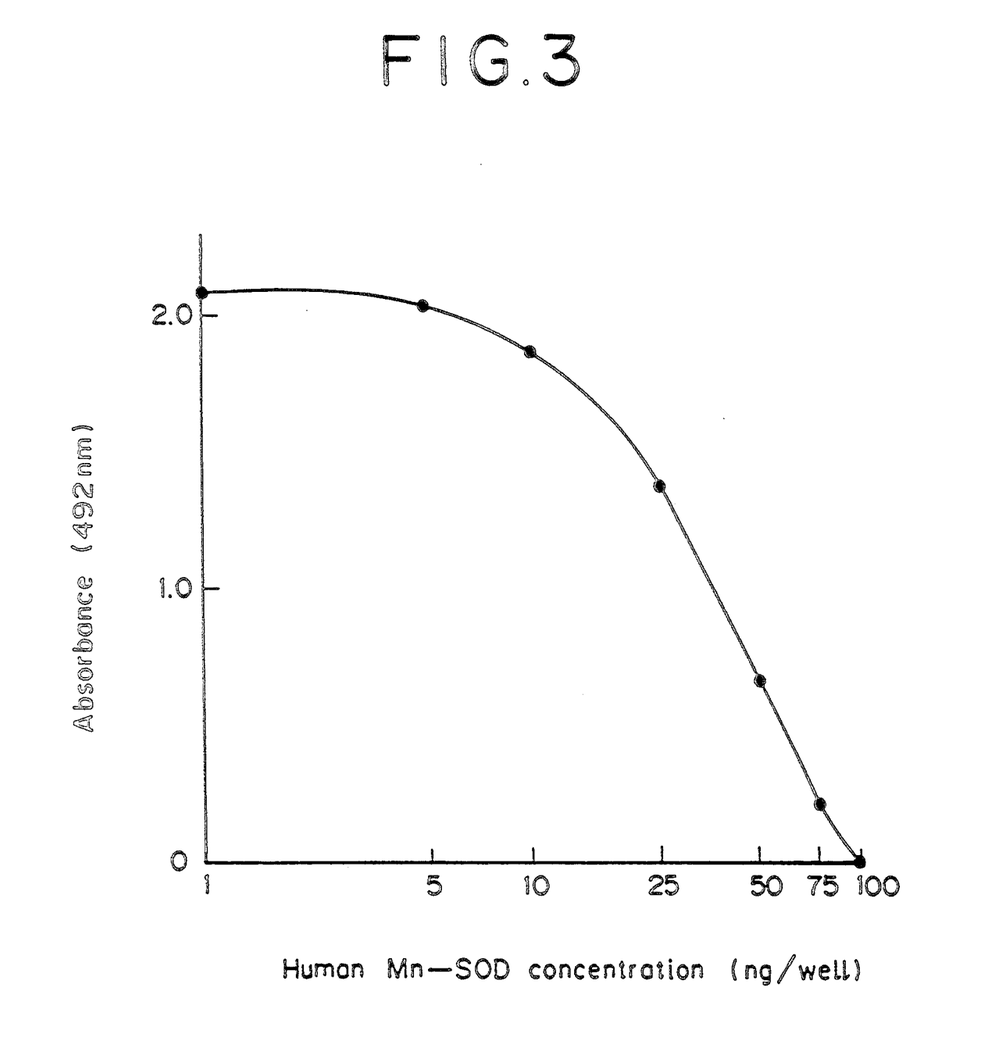
FIG. 3 shows the standard curve of human Mn-SOD prepared by use of the "synthetic peptide" solution C in the assay kit of the present invention in the assay method of human Mn-SOD of the present invention.
Figure 4:
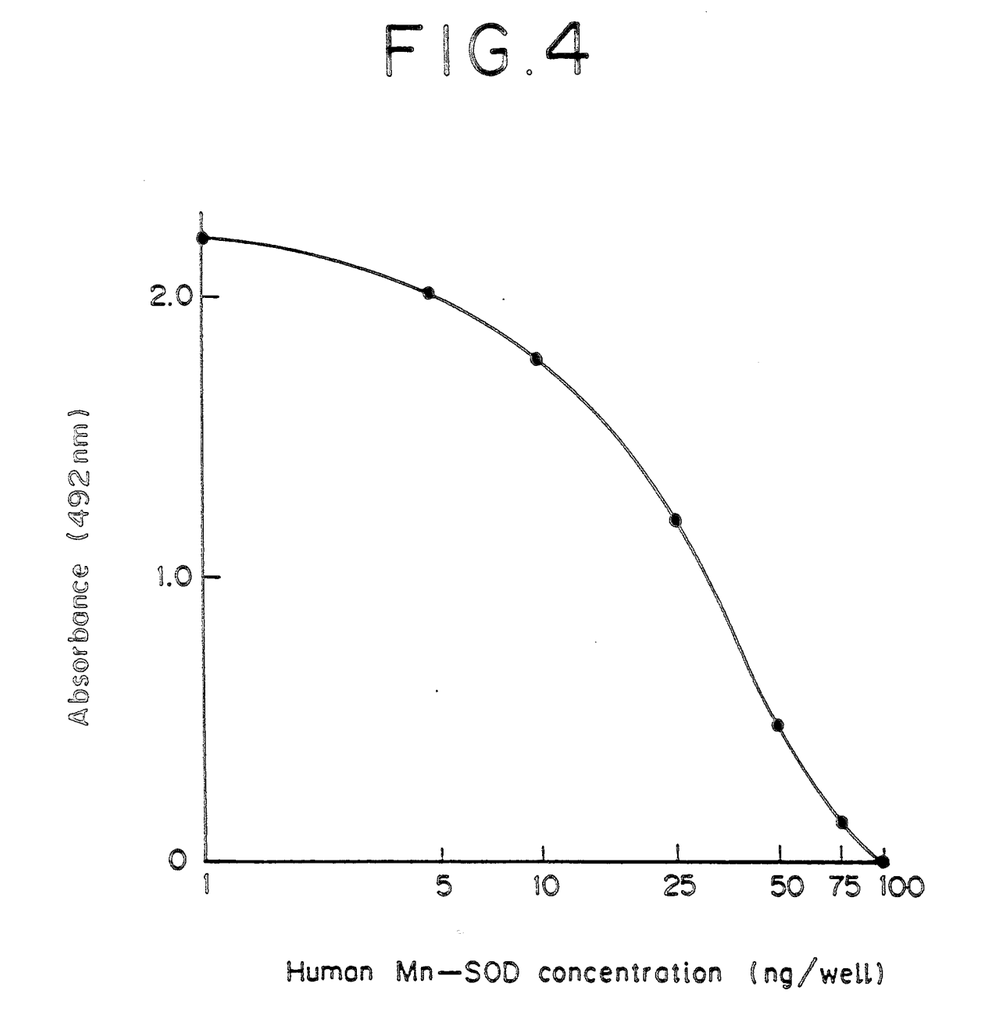
FIG. 4 shows the standard curve of human Mn-SOD prepared by use of the "synthetic peptide" solution D in the assay kit of the present invention in the assay method of human Mn-SOD of the present invention.
Figure 5:
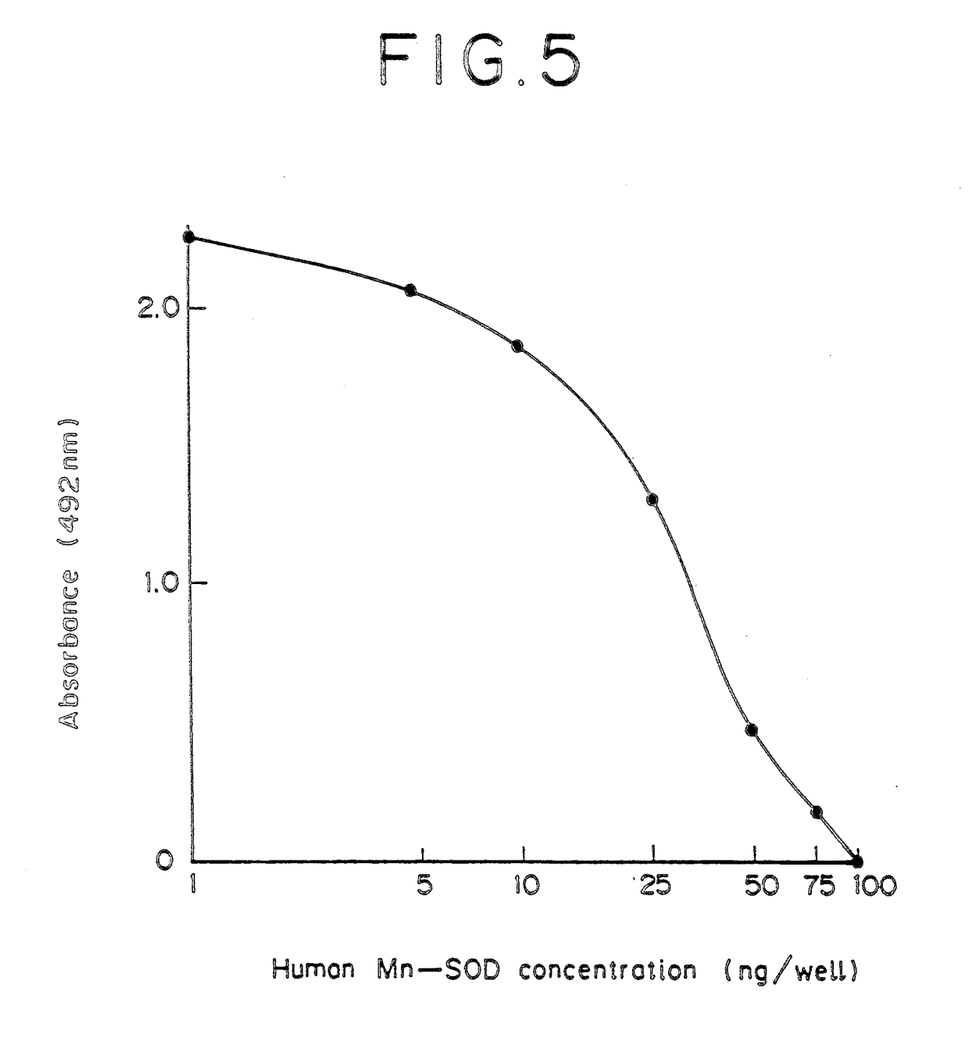
FIG. 5 shows the standard curve of human Mn-SOD prepared by use of the "synthetic peptide" solution E in the assay kit of the present invention in the assay method of human Mn-SOD of the present invention.
Figure 6:
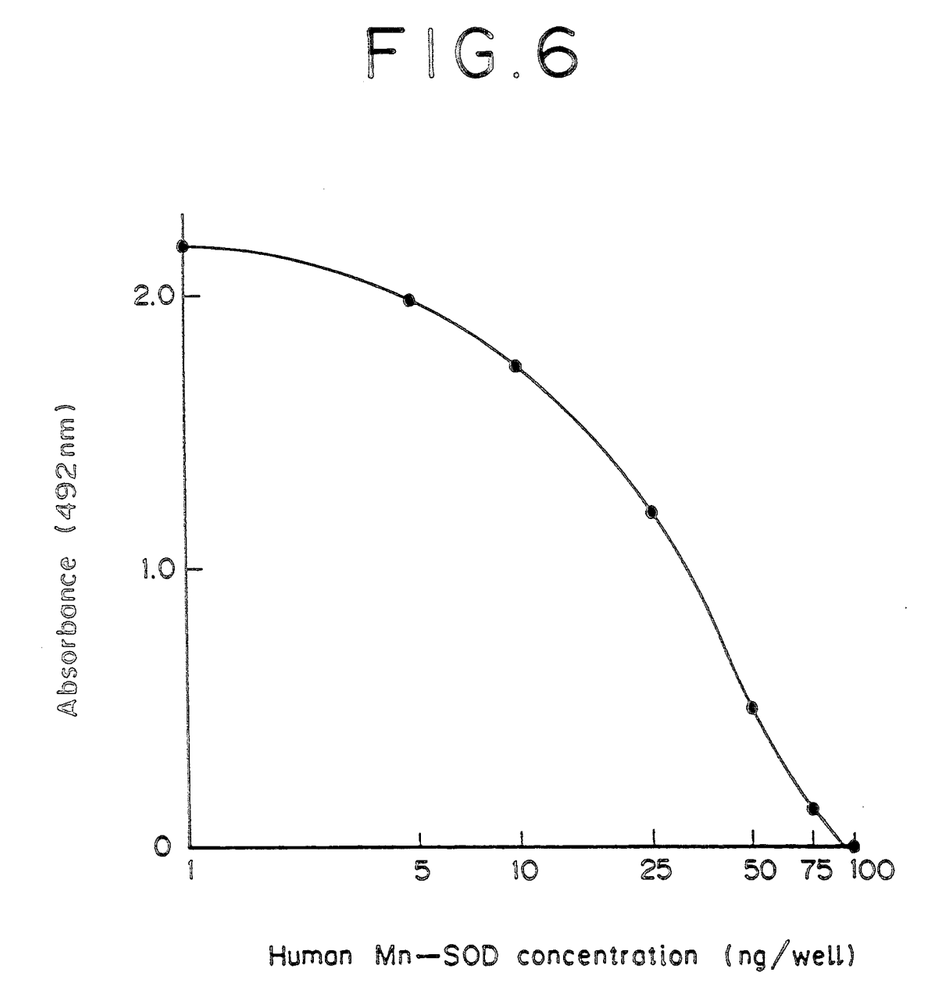
FIG. 6 shows the standard curve of human Mn-SOD prepared by use of the "synthetic peptide" solution F in the assay kit of the present invention in the assay method of human Mn-SOD of the present invention.
Figure 7:
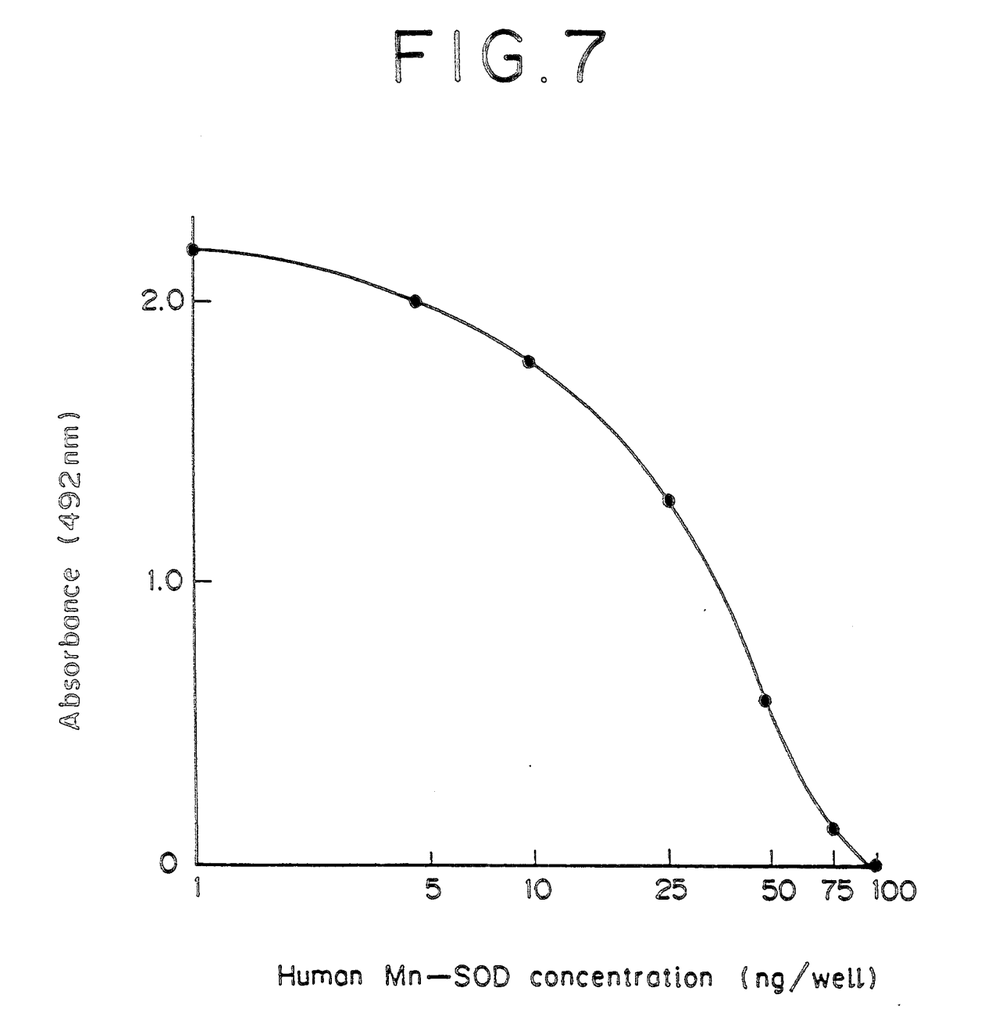
FIG. 7 shows the standard curve of human Mn-SOD prepared by use of the "synthetic peptide" solution G in the assay kit of the present invention in the assay method of human Mn-SOD of the present invention.
Figure 8:
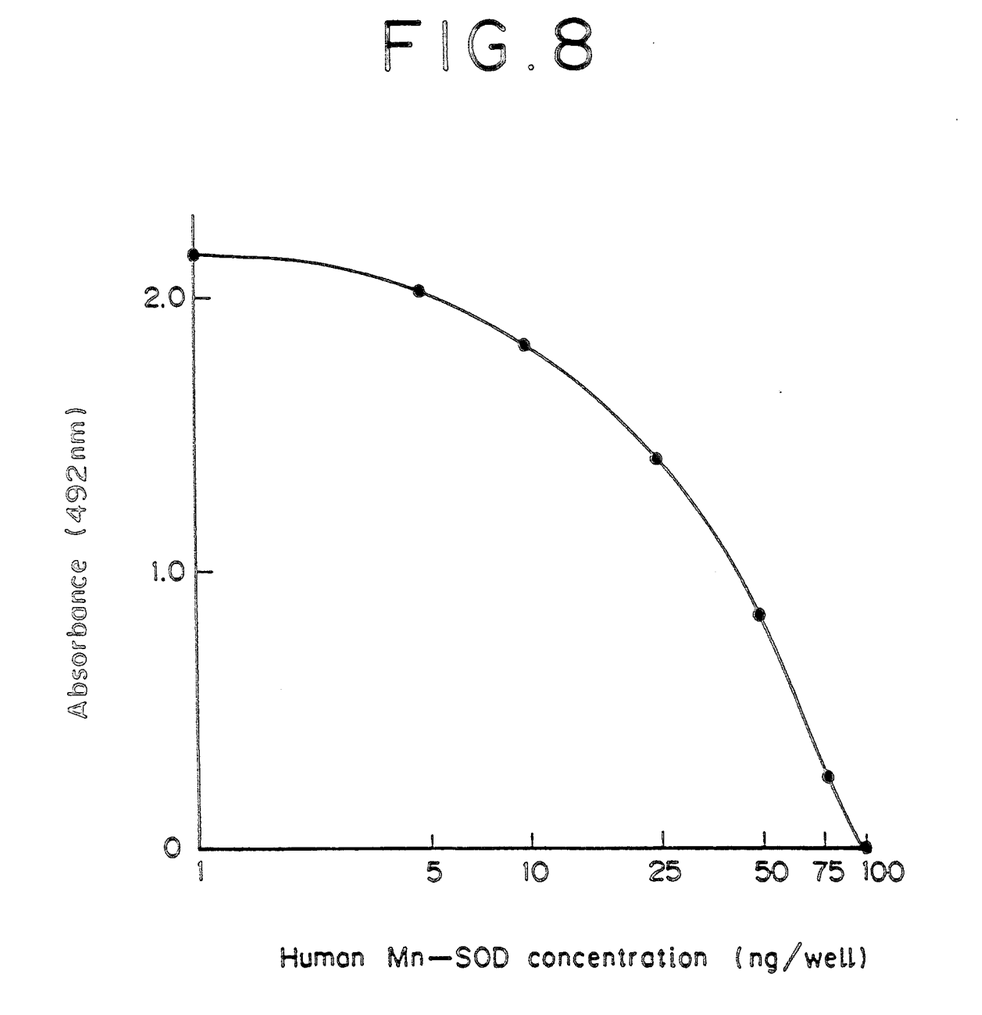
FIG. 8 shows the standard curve of human Mn-SOD prepared by use of the "synthetic peptide" solution H in the assay kit of the present invention in the assay method of human Mn-SOD of the present invention.
Figure 9:
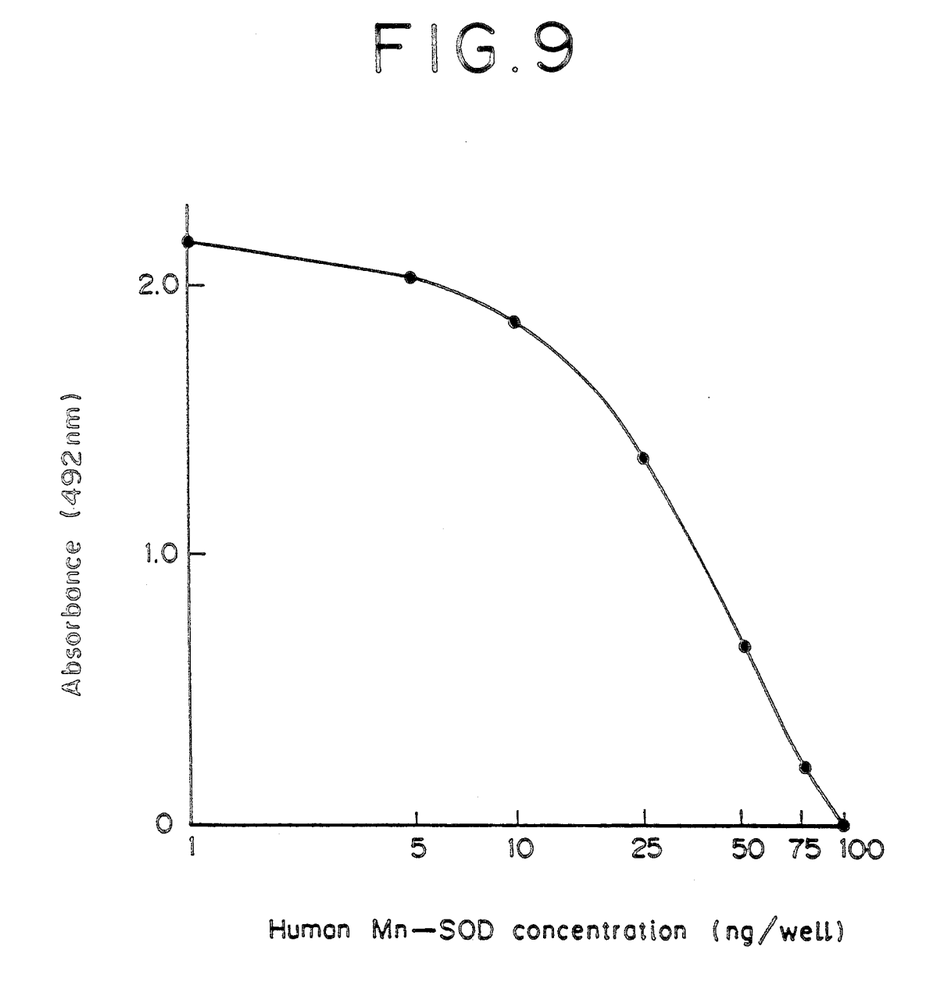
FIG. 9 shows the standard curve of human Mn-SOD prepared by use of the "synthetic peptide" solution I in the assay kit of the present invention in the assay method of human Mn-SOD of the present invention.
Figure 10:
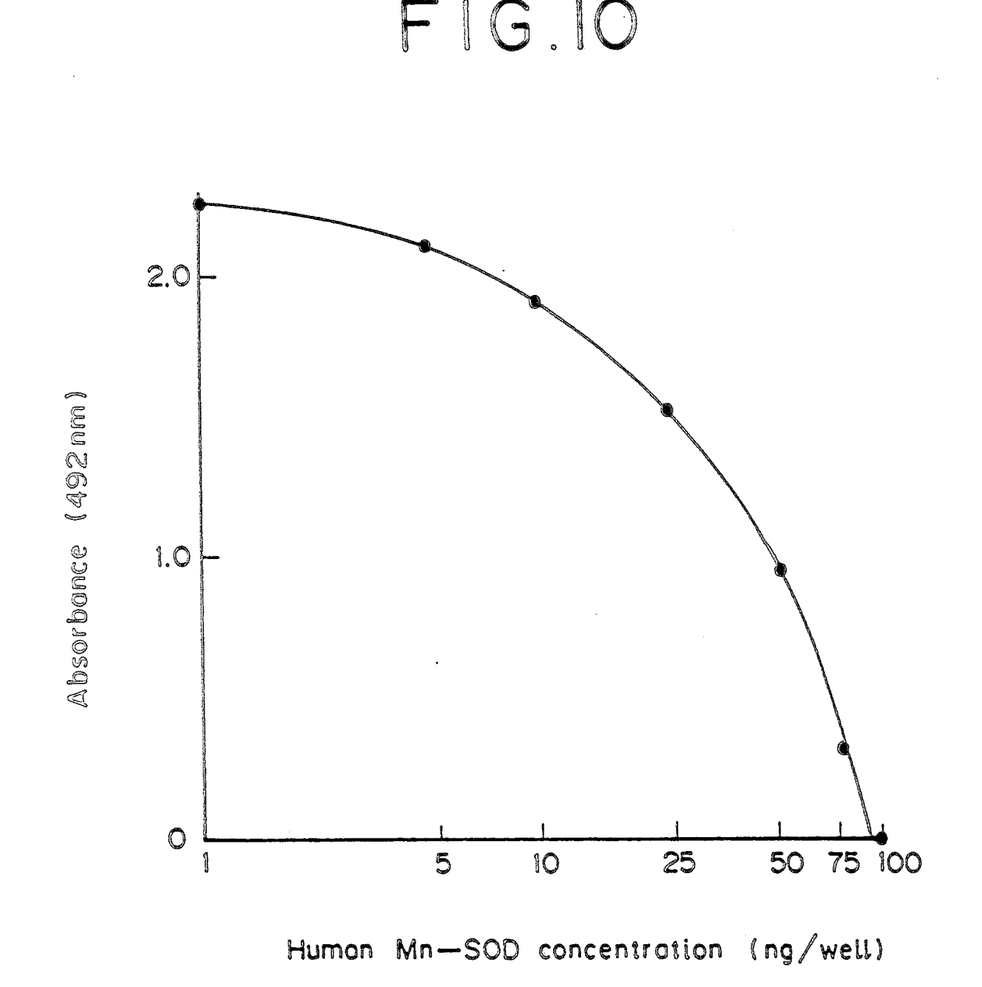
FIG. 10 shows the standard curve of human Mn-SOD prepared by use of the "synthetic peptide" solution J in the assay kit of the present invention in the assay method of human Mn-SOD of the present invention.

By use of the respective "synthetic peptide" of Examples 1 to 6 (a, b, c, d, e and f), the respective "synthetic peptide" solutions (A comprising only a; B comprising only b; C comprising only c; D comprising only d; E comprising only e; F comprising only f; G comprising equal weights of a and b; H comprising equal weights of c and d; I comprising equal weights of e and f; J comprising equal weights of b, d and f) (20 μg/ml, dissolved with PBS of pH 7.4) were prepared, which were apportioned each in 50 μl onto a 96-well flat bottom plate for immunoassay (microplate made of polystyrene of Nunc) which is the carrier, and left to stand stationarily at 37° C. for 20 hours to have the synthetic peptide immobilized on each well. Next, for removing the synthetic peptide not immobilized on the carrier, each well was washed with a washing solution comprising PBS containing 0.05% of Tween 20. Further, for prevention of nonspecific adsorption of human Mn-SOD and the monoclonal antibody (PG11), each 200 μl of PBS containing 0.5% of OVA (ovalbumin) was apportioned into each well and left to stand stationarily at room temperature for 30 minutes. Next, after washing with the same washing solution, "standard human Mn-SOD solutions" (20, 100, 200, 500, 1000, 1500, 2000 or 3000 ng/ml, dissolved with PBS) were prepared and each 50 μl was apportioned into each well, and further into each well of those was apportioned each 50 μl of the enzyme-labelled monoclonal antibody obtained in Example 2 (solution diluted to 250 folds with PBS), followed immediately by stirring by a plate mixer for 5 minutes and leaving to stand stationarily at 37° C. for one hour. Next, after washing with the same washing solution, into each well was apportioned each 100 μl of "substrate solution" (10 mg of o-phenylenediamine and 5 μl of 35% $H_2O_2$ dissolved in 25 ml of 0.1M citrate buffer of pH 5.0) and left to stand stationarily at room temperature for 15 minutes under light shielding. Finally, further each 50 μl of 2N sulfuric acid was apportioned to stop the enzyme reaction, and the absorbance of each solution after stopping of the reaction at 492 nm was measured by use of a microplate photometer to prepare standard curves. The standard curves when using the "synthetic peptide" solutions of A, B, C, D, E, F, G, H, I and J are shown respectively in FIG. 1, FIG. 2, FIG. 3, FIG. 4, FIG. 5, FIG. 6, FIG. 7, FIG. 8, FIG. 9 and FIG. 10.

Next, by use of a sample containing 25 ng as calculated of human Mn-SOD in 50 μl of 0.1% BSA (bovine serum albumin) solution in place of the "standard human Mn-SOD solution" as described above, its measured value was determined. As the result, the measured values when employing the "synthetic peptide" solutions of A, B, C, D, E, F, G, H, I and J were respectively 28, 26, 22, 26, 25, 24, 28, 27, 23, 27 ng. Thus, calculated values and measured values were found to be substantially identical.

According to the present invention, by use of the assay kit of human Mn-SOD comprising essentially the "synthetic peptide" and the enzyme-labelled monoclonal antibody of the present invention, human Mn-SOD can be assayed easily, rapidly and at high sensitivity.

We claim:

1. Monomeric synthetic peptide and dimeric synthetic peptide consisting essentially of an amino acid sequence represented by the formula:

wherein X represents a residue comprising a 0-to-10-amino-acid sequence from the carboxy end of human Mn-SOD; and Asn is aspartic acid; Val is valine, Thr is threonine, Glu is glutamic acid, Arg is arginine, Tyr is tyrosine, Met is methionine, Ala is alanine, Cys is cysteine and Lys is lysine.

2. The synthetic peptide according to claim 1, wherein said synthetic peptide consisting essentially of:

wherein Asn, Val, Thr, Glu, Arg, Tyr, Met, Ala, Cys and Lys are as defined above and Ile represents isoleucine and Trp represents tryptophan.

* * * * *